(12) United States Patent
Foolad

(10) Patent No.: US 8,524,992 B2
(45) Date of Patent: Sep. 3, 2013

(54) HIGH LYCOPENE CONTENT TOMATO PLANTS AND MARKERS FOR USE IN BREEDING FOR SAME

(71) Applicant: The Penn State Research Foundation, University Park, PA (US)

(72) Inventor: Majid R. Foolad, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/668,859

(22) Filed: Nov. 5, 2012

(65) Prior Publication Data

US 2013/0074204 A1    Mar. 21, 2013

Related U.S. Application Data

(63) Continuation of application No. 12/405,572, filed on Mar. 17, 2009, now abandoned.

(60) Provisional application No. 61/037,542, filed on Mar. 18, 2008.

(51) Int. Cl.
| | | |
|---|---|---|
| *A01H 1/00* | (2006.01) | |
| *A01H 5/08* | (2006.01) | |
| *C07H 21/04* | (2006.01) | |
| *C07K 14/415* | (2006.01) | |

(52) U.S. Cl.
USPC ........ 800/317.4; 435/6.1; 435/6.11; 435/411; 530/370; 536/23.1; 800/260

(58) Field of Classification Search
USPC ........ 435/6.1, 6.11, 411; 530/370; 536/23.1; 800/317.4; Plt./261
See application file for complete search history.

(56) References Cited

U.S. PATENT DOCUMENTS 4,326,358 A    4/1982    Lawrence et al.

FOREIGN PATENT DOCUMENTS

| WO | WO 03/057917 | 7/2003 |
|---|---|---|
| WO | WO 2005/072515 A1 | 8/2005 |

OTHER PUBLICATIONS

Chen et al., Mapping of QTLs for lycopene and other fruit traits in a *Lycopersicon esculentum* L. pimpinellifolium cross and comparison of QTLs across tomato species, Molecular Breeding 5:283-299, 1999.

Penn State Research Foundation, PCT/US09/37410, Written Opinion of the International Preliminary Examining Authority, dated Oct. 18, 2011, 7 pages.

*Primary Examiner* — Phuong Bui

(74) *Attorney, Agent, or Firm* — McKee, Voorhees & Sease, P.L.C.

(57) ABSTRACT

*Solanum pimpinellifolium* plants which are exceptionally high in fruit lycopene content (~300-390 μg lycopene/g fresh fruit) are disclosed herein, which may be used in plant breeding to make the tomato plants of the present invention. The invention also discloses genetic markers, which are associated with the trait which may be used in marker-assisted selection for development of plants, lines, or varieties with the trait.

12 Claims, No Drawings

HIGH LYCOPENE CONTENT TOMATO PLANTS AND MARKERS FOR USE IN BREEDING FOR SAME

CROSS-REFERENCE TO RELATED APPLICATIONS

This application is a Continuation Application of U.S. Ser. No. 12/405,572 filed Mar. 17, 2009 now abandoned, which claims priority under 35 U.S.C. §119(e) to provisional application Ser. No. 61/037,542 filed Mar. 18, 2008, herein incorporated by reference in its entirety.

GRANT REFERENCE

This invention was made with government support under Hatch Act Project No. PEN03769, awarded by the United States Department of Agriculture (USDA). The government has certain rights in the invention

FIELD OF THE INVENTION

The present invention relates to the field of agriculture, and to new and distinct inbred lines and hybrids of tomato (*Solanum lycopersicum*), and to method of making and using such inbred lines and hybrids. The invention also relates to genetic markers and QTLs which may be used for breeding techniques to incorporate higher lycopene content into tomato, and other plant species.

BACKGROUND OF THE INVENTION

The cultivated tomato, *Solanum lycopersicum* L., a fruit that is often treated as a vegetable, is widely grown around the world and constitutes a major agricultural industry. Worldwide, it is the second most consumed vegetable after potato (FAOSTAT 2005) and unquestionably the most popular garden crop. In the U.S., it is the third most economically important vegetable (with a total farm value of $2.062 billion) following potato ($2.564 B) and lettuce ($2.064 B) (USDA 2005; worldwide web at www.usda.gov/nass/pubs/agr05/agstats2005.pdf. In addition to tomatoes that are eaten directly as raw vegetable or added to other food items, a variety of processed products such as paste, whole peeled tomatoes, diced products, and various forms of juice, sauces and soups have gained significant acceptance. There are more varieties of tomato sold worldwide than any other vegetable. Although a tropical plant, tomato is grown in almost every corner of the world from the tropics to within a few degrees of the Arctic Circle. It is grown in greenhouses where outdoor production in restricted due to cool temperatures. Major tomato producing countries in descending orders include China, USA, India, Turkey, Egypt and Italy (worldwide web at faostat.fao.org). Other leading countries include Spain, Brazil, Iran, Mexico, Greece and Russia. In North America, production occurs in the U.S., Canada and Mexico, comprising a total of 310,000 ha. In 2004, the total harvested area in the U.S. was estimated to be 170,808 ha (50,560 ha fresh market and 120,248 ha processing tomatoes) with a total farm value of ~$2.06 B ($1.34 B fresh market and $0.72 B processing) (USDA 2005; worldwide web at nass.usda.gov:8080/OuickStats/index2.jsp). California and Florida are by far the leading producers of processing and fresh market tomatoes, respectively (USDA 2005). Worldwide, tomatoes are an important part of a diverse and balanced diet (Willcox et al. 2003). By virtue of volume consumed, tomato and tomato products contribute significantly to the dietary intake of vitamins A and C as well as essential minerals and other nutrients. In the U.S. diet, for example, tomato ranks first among all fruits and vegetables as a source of vitamins and minerals (Rick 1980) and phenolic antioxidants (Vinson et al. 1998). Also, fresh and processed tomatoes are the richest sources of the anti-oxidant lycopene (Nguyen and Schwartz 1999), which can protect cells from oxidants that have been linked to cancer (Giovannucci 1999) (see below).

In addition to the appearance and taste, consumers' perceptions of fruit quality are now influenced by perceived health benefits. Fruit color is a quality characteristic that has received intensive attention by fresh-market and processing tomato industries as well as consumers. The final color in tomato fruit is conditioned by the total amount and proportion of different carotenoids. Lycopene is the red pigment and a major carotenoid in tomato. In processing tomato, fruit color influences the grades and standards of the processed commodity. In fresh market tomato, fruit color has significant effect on its marketability. The attention to fruit color has recently been on the rise due to the increasing knowledge of the health benefits of different carotenoids. Fresh tomatoes and tomato products are presently major sources of LYC, a potent natural antioxidant that is increasing in demand. Numerous epidemiological and intervention studies have demonstrated that dietary intake of LYC-rich foods results in decreased incidence of certain cancers, including the prostate, lung, mouth, and colon cancers, and the coronary heart diseases, cataracts and may be macular degeneration (Gerster 1997; Giovannucci 1999; Giovannucci and Clinton 1998; Sies and Stahl 1998; Tsubono et al. 1999; Willcox et al. 2003). This attention to lycopene is well deserved, as its antioxidant capacity is roughly twice that of β-carotene (Di Mascio et al. 1990). As the scientific community has become more aware of the impact of carotenoids on human health, attention has shifted to increasing tomato fruit lycopene content.

Although tomato is the richest source of lycopene among all fruits and vegetables, its concentration in the fruit of commercial cultivars is rather low, on average ranging from 30 to 60 Jig lycopene/g fresh tomato tissue. An increase in the concentration of lycopene in commercial cultivars of tomatoes has been an interest of plant breeders, growers and processors. Previously, spontaneous mutations contributing to high lycopene content were identified in *S. lycopersicum*, including two recessive mutant genes, hp1 (high pigment 1) (Yen et al. 1997) and hp2 (van Tuinen et al. 1997) which were mapped to tomato chromosomes 2 and 1, respectively. The hp genes increase the total fruit carotenoids, including β-carotene (Palmieri et al. 1978). These genes were subsequently introgressed into several tomato cultivars (Soressi 1975; Thompson et al. 1962). However, the adverse pleiotropic effects of hp genes, such as slow germination and seedling growth, seedling mortality, inferior leaf coverage, brittle stems, low yield, reduced total acidity and soluble solids content (SSC), high sensitivity to various pathogens and premature defoliation, have prohibited widespread commercial use of these genes (Wann 1995). Efforts to reduce these negative effects have largely failed and thus, currently only a handful of lycopene-rich tomato cultivars carrying hp1 or hp2 are being used in intensive production. Furthermore, as both of these genes are recessive in nature, they are undesirable for production of hybrid cultivars with high fruit lycopene content. Additional neutral pleiotropic effects of these genes include accumulation of anthocyanin in hypocotyls, shorter and darker hypocotel, and dark green immature fruit.

In addition to hp1 or hp2, a crimson gene ($og^c$, cr) has been identified and mapped to tomato chromosome 6 which increases fruit lycopene content of the cultivated tomato by about 25%, though at the expense of β-carotene (Ronen et al. 2000; Thompson et al. 1967). This gene has been incorporated into many recent tomato breeding lines and cultivars, and commercial hybrids containing this gene are available. The $og^c$ is physically tightly linked to a self-pruning gene (sp) gene on chromosome 6, and thus high lycopene plants (homozygous for $og^c$) are all determinate in nature. There has been no report of an indeterminate plant ($sp^+sp^+$) with high lycopene content (i.e. with $og^c$ gene). This is a major limitation of this technology.

It is an objective of the present invention to disclose a novel *Solanum pimpinellifolium* accession designated as LA2093 previously designated LAxxxx or PSPL125 that can be used as a source of high fruit lycopene content. The fruit lycopene concentration of this accession is as high as 390 μg/g fresh tomato tissue. It is a further objective of this invention to provide *Solanum lycopersicum* plants which are high in fruit lycopene content, in the range of 100-200 μg/g fresh tomato tissue.

It is yet another object of the invention to provide genetic markers which may be used for marker assisted selection to incorporate the high lycopene content trait into tomato plants and other *Solanum* species.

SUMMARY OF THE INVENTION

The present invention discloses new and distinct inbred tomato lines and hybrids of tomato (*Solanum lycopersicum*) with high lycopene content. The present invention also discloses methods of making and using such inbred lines and hybrids.

In one embodiment the invention discloses a few QTLs which are associated with high lycopene content in the tomato inbred lines developed at Penn State and in a closely related wild species. According to the invention a QTL has been identified on chromosome 7 between publically available markers cTOS19O5 and cLEN14F9 and one on chromosome 12 between publically available markers OH275 and T0800, which may be used in marker-assisted selection of plants to be used for breeding purposes. According to the invention, the QTLs mapped to chromosome 7 and 12 have been identified with high lycopene content. Publically available markers cTOS19O5 and cLEN14F9 and OH275 and T0800 have been shown to map close to these QTLs and these markers may be used in backcross breeding to select for the high lycopene trait in tomatoes. The publicly available data base worldwide web at sgn.cornell.edu may be used to identify the sequence of the public markers used herein.

In one embodiment, the present invention discloses new and distinct inbred tomato lines for tomatoes designated PSU high lycopene cherry tomato, PSCH-2 previously designated xxxx, or PSPL125; PSU high lycopene grape tomato, PSGR-23 (previously designated YYYY, and PSU high lycopene plum tomato, PSPL-1, (previously designated ZZZZ. This invention also discloses seeds of said inbred tomato lines, plants of the inbred tomato lines, and parts of said plants, such as pollen, ovule or fruit. The present invention also discloses methods for producing a tomato plant produced by crossing a plant of said inbred line with itself or another tomato line.

This invention also relates to methods for producing other inbred tomato lines derived from inbred tomato lines of the invention and to the inbred tomato lines derived by the use of those methods. This invention further relates to hybrid tomato seeds and plants produced by crossing inbred tomato line of the invention with another tomato line.

In one embodiment, this invention also discloses seeds of such a tomato hybrid, plants of said tomato hybrid, and parts of said plants, such as pollen, ovule or fruit. The present invention also discloses methods for producing a tomato plant comprising crossing tomato hybrid with itself or another tomato line.

The invention further discloses method of producing seed of a plant of the present invention comprising crossing an inbred line or hybrid of the present invention with itself or with another line or hybrid, and seed produced by such method. The invention also discloses methods of vegetatively propagating a plant of the present invention, and to plants produced by such methods. This invention also discloses methods for producing a fruit of a tomato plant of the present invention and to fruits produced by such methods.

A tomato plant of the invention may further comprise a cytoplasmic factor or other factor that is capable of conferring male sterility. Male sterility may also be provided by nuclear genes such as the recessive ms gene.

In another aspect, the present invention provides regenerable cells for use in tissue culture. The tissue culture will preferably be capable of regenerating plants having the physiological and morphological characteristics of the foregoing tomato plants, and of regenerating plants having substantially the same genotype as the foregoing tomato plants. Preferably, the regenerable cells in such tissue cultures will be embryos, protoplasts, meristematic cells, callus, pollen, leaves, anthers, stems, petioles, roots, root tips, fruits, seeds, flowers, cotyledons, hypocotyls or the like. Still further, the present invention provides tomato plants regenerated from the tissue cultures of the invention.

In another aspect, the present invention provides for single gene converted plants of inbred tomato lines of the invention, or hybrid lines of the invention. The single transferred gene may preferably be a dominant or recessive allele. Preferably, the single transferred gene will confer such trait as male sterility, herbicide resistance, insect resistance, resistance for bacterial, fungal, or viral disease, male fertility, improved harvest characteristics, enhanced nutritional quality, improved processing characteristics. The single gene may be a naturally occurring tomato gene or a transgene introduced through genetic engineering techniques. The present invention also discloses methods for producing a tomato plant containing in its genetic material one or more transgenes and to the transgenic tomato plants produced by that method. The invention further provides methods for developing tomato plant in a tomato plant breeding program using plant breeding technique including recurrent selection, backcrossing, pedigree breeding, restriction fragment length polymorphism enhanced selection, genetic marker enhanced selection and transformation. Seeds, tomato plant, and parties thereof produced by such breeding methods are also part of the invention.

DEFINITIONS

In the description and tables that follow, a number of terms are used. The terms are used to provide a clear understanding of the specifications and are used in accordance with the terminology defined in the UPOV Technical Guidelines for tomato (TG/4417), which is incorporated herein by reference in its entirety. The following definitions are also provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid F1 with one of the parental genotype of the F1 hybrid.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Soluble Solids. Soluble solids refer to the percent of solid materials found in the fruit tissue, the vast majority of which is sugars. Soluble solids are directly related to finished processed product yield of pastes and sauces. Soluble solids are estimated with a refractometer, and measured as degrees brix.

pH: the pH is a measure of acidity.

Viscosity: The viscosity or consistency of tomato products is affected by the degree of concentration of the tomato, the amount of and extent of degradation of pectine, the size, shape and quality of the pulp, and probably to a lesser extent, by the proteins, sugars and other soluble constituents. The viscosity is measured in Bostwick centimeters by using instruments such as a Bostwick Consistometer.

As used herein, the term "tomato" means any plant, line or population of ycopersicon including but not limited to *Lycopersicon esculentum* (syn. *Solanum lycopersicum*), *Lycopersicon esculentum* var. *cerasiforme* (syn. *Solanum lycopersicum* var. *cerasiforme*), *Lycopersicon cheesmaniae* (syn. *Solanum cheesmaniae*), *Lycopersicon chilense* (syn. *Solanum chilense*), *Lycopersicon chmielewskii* (syn. *Solanum chmielewskii*), *Lycopersicon hirsutum* (syn. *Solanum habrochaites*), *Lycopersicon parviflorum* (syn. *Solanum neorickii*), *Lycopersicon pennellii* (syn. *Solanum pennellii*), *Lycopersicon peruvianum* (syn. *Solanum 'N peruvianum'*), *Lycopersicon pimpinellifolium* (syn. *Solanum lycopersicum*), *Solanum juglandifolium*, *Solanum ochranthum*, *Solanum sitiens*, or *Solanum lycopersicoides*. Although Linnaeus first categorized the modern tomato as a *Solanum*, its scientific name for many years has been *Lycopersicon esculentum*. Similarly, the wild relatives of the modern tomato have been classified within the *Lycopersicon* genus, like *L. pennellii*, *L. hirsutum*, *L. peruvianum*, *L. chilense*, *L. parviflorum*, *L. chmielewskii*, *L. cheesmanii*, *L. cerasiforme*, and *L. pimpinellifolium*. Over the past several years, there has been debate among tomato researchers and botanists whether to reclassify the names of these species. The newly proposed scientific name for the modern (cultivated) tomato is *Solanum lycopersicum*. Similarly, the names of the wild species may be altered. *L. pennellii* may become *Solanum pennellii*, *L. hirsutum* may become *S. habrochaites*, *L. peruvianum* may be split into *S. 'N. peruvianum'* and *S. 'Callejon de Huayles,' S. peruvianum*, and *S. corneliomuelleri*, *L. parviflorum* may become *S. neorickii*, *L. chmielewskii* may become *S. chmielewskii*, *L. chilense* may become *S. chilense*, *L. cheesmaniae* may become *S. cheesmaniae* or *S. galapagense*, and *L. pimpinellifolium* may become *S. pimpinellifolium* (Solanacea Genome Network (2005) Spooner and Knapp; worldwide web at www.sgn.cornell.edu/help/about/solanum nomenclature.html).

As used herein, the term "variety" or "cultivar" means a group of similar plants that by structural or genetic features and/or performance can be distinguished from other varieties within the same species.

The term "QTL" is used herein in its art-recognized meaning The term "QTL associated with high lycopene content in tomato" as well as the shorter term "QTL for lycopene content" refer to a region located on a particular chromosome of tomato that is associated with at least one gene that encodes for higher than average lycopene content or at least a regulatory region, i.e. a region of a chromosome that controls the expression of one or more genes involved in lycopene content. A QTL may for instance comprise one or more genes of which the products confer the altered lycopene content. Alternatively, a QTL may for instance comprise regulatory genes or sequences of which the products influence the expression of genes on other loci in the genome of the plant thereby conferring the lycopene content. The QTLs of the present invention may be defined by indicating their genetic location in the genome of the respective wild *Lycopersicon* accession using one or more molecular genetic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a general rule, one centimorgan (cM) is equal to 1% recombination between loci (markers). When a QTL can be indicated by multiple flanking markers the genetic distance between the end-point markers is indicative of the size of the QTL.

DETAILED DESCRIPTION OF THE INVENTION

The present invention discloses new and distinct inbred tomato lines and hybrids of tomato (*Lycopersicon esculentum*) with higher than average lycopene content. The invention discloses publically available genetic markers which are linked to various QTLs which are associated with increased lycopene content in plants.

The present invention also discloses methods of making and using such inbred lines and hybrids. In one embodiment, the present invention discloses a new and distinct inbred tomato line, designated PSU high lycopene cherry tomato, PSCH-2; PSU high lycopene grape tomato, PSGR-23; and PSU high lycopene plum tomato, PSPL-1.

In one embodiment, this invention also discloses tomato hybrid plants produced by crossing one of more of the inbred lines of the invention with a second inbred line In one embodiment, the tomato inbred lines and hybrids of the present invention are capable of producing a fruit, which has a higher than average lycopene content. As used herein higher lycopene content shall be interpreted to mean the average lycopene content of a plant, population or group of plants which have been selected for the QTL of the invention and as compared to a plant, population or group of plants that have not been so selected.

The tomato inbred lines and hybrid of the instant invention have shown uniformity and stability for all traits. The inbred lines of the present invention have been self-pollinated and planted for a sufficient number of generations, with careful attention to uniformity of plant type to ensure homozygosity and phenotypic stability. No variant traits have been observed or are expected. In one embodiment, the present invention discloses a method of producing seed of a tomato plant of the present invention comprising: a) growing a plant of the present invention; b) allowing said plant to self-pollinate; c) harvesting seeds from said plant.

The inbred lines of the instant invention have superior characteristics, and provide excellent parental lines in crosses for producing first generation ($F_1$) hybrid tomato. In one embodiment, the present invention also discloses a method of producing a hybrid tomato seed. In one embodiment, the method comprises crossing a plant of an inbred tomato line of the instant invention with a plant of another tomato line.

A tomato plant can also be propagated vegetatively. A part of the plant, for example a shoot tissue, is collected, and a new plant is obtained from the part. Such part typically comprises an apical meristem of the plant. The collected part is transferred to a medium allowing development of a plantlet, including for example rooting or development of shoots, or is grafted onto a tomato plant or a rootstock prepared to support growth of shoot tissue. This is achieved using methods well-known in the art. Accordingly, in one embodiment, a method of vegetatively propagating a plant of the present invention comprises collecting a part of a plant according to the present invention, e.g. a shoot tissue, and obtaining a plantlet from said part. In one embodiment, a method of vegetatively propagating a plant of the present invention comprises: a) collecting tissue of a plant of the present invention; b) rooting said proliferated shoots to obtain rooted plantlets. In one embodiment, a method of vegetatively propagating a plant of the present invention comprises: a) collecting tissue of a plant of the present invention; b) cultivating said tissue to obtain proliferated shoots; c) rooting said proliferated shoots to obtain rooted plantlets. In one embodiment, such method further comprises growing a plant from said plantlets. In one embodiment, a fruit is harvested from said plant.

The present invention also contemplates a tomato plant regenerated from a tissue culture of an inbred or hybrid plant of the present invention. As is well known in the art, tissue culture of tomato can be used for the in vitro regeneration of a tomato plant. [Reference: Kartha, K. K., Gamborg, O. L., Shyluk, J. P., and Constabel, F., Morphogenetic investigations on in vitro leaf cultures of tomato (*Lycopersicon esculentum* Mill. cv. Starfire) and high frequency plant regeneration, Z. Pflanzenphysiol., 77, 292, 1976.]

In one embodiment, the present invention discloses a method of producing a tomato fruit. In one embodiment, such method comprises growing a plant of the instant invention to produce a tomato fruit, and harvesting said tomato fruit. In one embodiment, the method further comprises packing said fruit in a suitable container. In one embodiment, the method further comprises shipping said fruit. In one embodiment, a fruit of a tomato plant of the present invention is used in fresh consumption or is processed.

The present invention relates in another aspect to a method for detecting a quantitative trait locus (QTL) associated with high fruit lycopene content in tomato. The method comprises the steps of crossing a high lycopene content wild-type donor tomato plant with a low (normal) lycopene content recipient modern tomato plant and produce F1 progeny (offspring); assaying the $F_1$ progeny for lycopene content in one or more offspring plants; self pollinating selected F1 progeny and subsequent filial progeny to produce segregating $F_2$, $F_3$, $F_4$, $F_5$, $F_6$, $F_7$, $F_8$, $F_9$ and $F_{10}$ generations; developing a genetic linkage map using molecular markers; conducting analysis to link the observed lycopene content to the presence of chromosomal markers of said donor tomato plant in said one or more offspring plants; and assigning to quantitative trait loci (QTLs) the contiguous markers on said map that are linked to an improved lycopene content.

In another aspect, the present invention relates to QTLs obtainable by a method for detecting QTLs for high lycopene content according to the invention as outlined herein. Such information is highly valuable in breeding programs, since combinations of these marker-linked QTLs may provide for high lycopene content or for proper inheritance of a resistance trait from one generation to another; such knowledge can facilitated the breeding progress.

Below is the information as to molecular markers flanking the two QTLs:
QTL on chromosome 7: cTOS19O5 and cLEN14F9.
QTL Chromosome 12: OH275 and T0800.

The present invention further relates to a QTL for lycopene content in tomato, wherein said QTL is selected from the group consisting of the QTLs on chromosomes 7 and 12. These QTLs are located on positions of the genome not previously identified or associated with lycopene content. Details of these QTLs are described in more detail herein below.

The alleles present on the positions of the genome indicated by these QTLs are an aspect of the present invention.

A QTL of the present invention may be in the form of an isolated, preferably double stranded nucleic acid sequence comprising said QTL or a high lycopene content-conferring part thereof. Very suitably, the size of the nucleic acid sequence, which may for instance be isolated from the chromosome of a suitable donor plant, may represent a genetic distance of 1-100 cM, preferably 10-50 cM on said chromosome. Said nucleic acid may comprise at least 50, more preferably at least 500, even more preferably at least 1000, still more preferably at least 10000 base pairs. One or more nucleic acid sequences comprising a QTL or according to the invention may in turn be comprised in a nucleic acid construct, said construct may further comprise regions that flank said one or more nucleic acid sequences and which regions are capable of being integrated into a suitable vector for transfer of said one or more nucleic acid sequences into a suitable recipient tomato plant. The vector may further comprise suitable promoter regions or other regulatory sequences. The QTLs may also be in a form present within the genome of a tomato plant.

The present invention relates in another aspect to a method for detecting a QTL for lycopene content, comprising detecting at least one marker selected from the group consisting of the markers on chromosomes 7 and 12 linked to two QTLs for high lycopene content in a tomato plant.

The present invention further relates to a method of producing a high lycopene content tomato plant. The method comprises the steps of detecting a QTL for high lycopene content in a donor tomato plant by performing any one of the methods for detecting a quantitative trait locus (QTL) for high lycopene content according to the invention, and transferring nucleic acid comprising at least one QTL thus detected, or a high lycopene content conferring part thereof, from said donor plant to a recipient tomato plant.

The transfer of nucleic acid comprising at least one QTL or a high lycopene content conferring part thereof may very suitably be performed by crossing said high lycopene donor tomato plant with a normal lycopene content tomato plant to produce offspring plants; and selecting from among the offspring plants a plant that comprises in its genome nucleic acid introgressed from said donor tomato plant, wherein said introgressed nucleic acid comprises at least one QTL for high lycopene content according to the invention, or a high lycopene-conferring part thereof. The presence in said introgressed nucleic acid of at least one QTL for high lycopene content according to the invention, or a high lycopene content-conferring part thereof, may suitably be detected by a method according to the present invention wherein at least one marker selected from the group consisting of the markers disclosed herein on chromosome 7 and chromosome 12.

A preferred selection method therefore comprises marker-assisted selection (MAS) (see e.g. Tanksley et al. 1998) of said introgressed DNA wherein one or more markers associated with said QTL are detected in offspring plants. MAS may for instance be performed by isolating genetic material from said offspring plants and determining the presence therein, by molecular techniques, of one or more donor plant markers. Alternatively, molecular marker detection methods may be used without prior isolation of genetic material. Optionally, in addition to the marker detection, a phenotypic test on lycopene content may be performed in order to select suitable plants. A very suitable test therefore is the quantitative bioassay as described herein. The confirmation of the presence of at least one marker from a QTL for high lycopene content in combination with the establishment of the presence of a high lycopene phenotype provides evidence for the successful transfer of nucleic acid comprising at least one QTL, or a high lycopene content-conferring part thereof, from the donor plant to the recipient plant. Molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed tomato plants, using transformation methods as described below to incorporate transgenes into the genetic material of the tomato plant(s).

Expression Vectors for Tomato Transformation

Marker Genes—Expression vectors include at least one genetic marker, operably linked to a regulatory element (a promoter, for example) that allows transformed cells containing the marker to be either recovered by negative selection, i e , inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptll) gene, isolated from transposon Tn5, which when placed under the control of plant regulatory signals confers resistance to kanamycin. Fraley et al., Proc. Natl. Acad. Sci. U.S.A., 80:4803 (1983), Aragao F. J. L., et al., Molecular Breeding 4:6 491-499 (1998). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990), Hille et al., Plant Mol. Biol. 7:171 (1986).

Other selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988), Saker M. M., et al, Biologia Plantarum 40:4 507-514 (1998), Russel, D. R., et al, Plant Cell Report 12:3 165-169 (1993).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol, acetyltransferase. Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), DeBlock et al., EMBO J. 3:1681 (1984), Grossi M. F., et al., Plant Science 103:2 189-198 (1994), Lewis M. E., Journal of the American Society for Horticultural Science 119:2 361-366 (1994), Zhang et al., Journal of the American Society for Horticultural Science 122:3 300-305 (1997).

Recently, in vivo methods for visualizing GUS activity that do not require destruction of plant tissue have been made available. Molecular Probes publication 2908, Imagene Green, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263: 802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in tomato. Optionally, the inducible promoter is operably linked to a nucleotide sequence encoding a signal sequence which is operably linked to a gene for expression in tomato. With an inducible promoter the rate of transcription increases in response to an inducing agent.

Any inducible promoter can be used in the instant invention. See Ward et al., Plant Mol. Biol. 22:361-366 (1993). Exemplary inducible promoters include, but are not limited to, that from the ACEI system which responds to copper (Meft et al., PNAS 90:4567-4571 (1993)); In2 gene from maize which responds to benzene sulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227: 229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter is operably linked to a gene for expression in tomato or the constitutive promoter is operably linked to a nucleotide sequence encoding a signal sequence which is operably linked to a gene for expression in tomato.

Many different constitutive promoters can be utilized in the instant invention. Exemplary constitutive promoters include, but are not limited to, the promoters from plant viruses such as the .sup.35S promoter from CaMV (Odell et al., Nature 313: 810-812 (1985), Aragao et al., Genetics and Molecular Biology 22:3, 445-449 (1999) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)).

The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT Application No. WO96/30530.

C. Tissue-Specific or Tissue-Preferred Promoters

A tissue-specific promoter is operably linked to a gene for expression in tomato.

Optionally, the tissue-specific promoter is operably linked to a nucleotide sequence encoding a signal sequence which is operably linked to a gene for expression in tomato. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11): 2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., "Structure and Organization of Two Divergent Alpha-Amylase Genes from Barley", Plant Mol. Biol. 9:3-17 (1987), Lerner et al., Plant Physiol. 91:124-129 (1989), Fontes et al., Plant Cell 3:483496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is tomato. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. *Tomato* encodes a protein kinase); Mindrinos et al., Cell 78:1089 (1994) (*Arabidopsis* RSP2 gene for resistance to *Pseudomonas syingae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt delta-endotoxin gene. Moreover, DNA molecules encoding delta-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., Plant Molec. Biol. 24:25 (1994), who disclose the nucleotide sequences of several *Clivia miniata* mannose-binding lectin genes.

D. A vitamin-binding protein such as avidin. See PCT Application No. US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotech. Biochem. 57:1243 (1993) (nucleotide sequence of Streptomyces nitrosporeus alpha-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT Application No. WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung tomato calmodulin cDNA clones, and Griess et al., Plant Physiol. 104:1467 (1994), who provide the nucleotide sequence of a maize calmodulin cDNA clone.

L. A hydrophobic moment peptide. See PCT Application No. WO95/16776 (disclosure of peptide derivatives of Tachyplesin which inhibit fungal plant pathogens) and PCT Application No. WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-beta, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Intl Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.
Q. A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10:1436 (1992). The cloning and characterization of a gene which encodes a tomato endopolygalacturonase-inhibiting protein is described by Toubart et al., Plant J. 2:367 (1992).
R. A development-arrestive protein produced in nature by a plant. For example, Logemann et al., Bioi/Technology 10:305 (1992), have shown that transgenic plants expressing the barley ribosome-inactivating gene have an increased resistance to fungal disease.

2. Genes that Confer Resistance to a Herbicide, for Example
A. A herbicide that inhibits the growing point or meristem, such as an imidazolinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.
B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and Streptomyces hygroscopicus phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. European Patent Application No. 0 333 033 to Kumada et al., and U.S. Pat. No. 4,975,374 to Goodman et al., disclose nucleotide sequences of glutamine synthetase genes which confer resistance to herbicides such as L-phosphinothricin. See also Russel, D. R., et al, Plant Cell Report 12:3 165-169 (1993). The nucleotide sequence of a phosphinothricin-acetyl-tran-sferase gene is provided in European Application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Accl-S1, Accl-S2 and Accl-S3 genes described by Marshall et al., Theor. Appl. Genet. 83:435 (1992).
C. A herbicide that inhibits photosynthesis, such as a triazine (psbA and gs+ genes) and a benzonitrile (nitrilase gene). Przibilla et al., Plant Cell 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as
A. Delayed and attenuated symptoms to Tomato Golden Mosaic Geminivirus (BGMV), for example by transforming a plant with antisense genes from the Brazilian BGMV. See Arago et al., Molecular Breeding. 1998, 4:6, 491-499.
B. Increased the tomato content in Methionine by introducing a transgene coding for a Methionine rich storage albumin (2S-albumin) from the Brazil nut as described in Arago et al., Genetics and Molecular Biology. 1999, 22:3, 445-449.

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., Science 227:1229 (1985). McClean, P., et al. Plant Cell Tissue Org. Cult. 24(2, February), 131-138 (1991), Lewis et al., Journal of the American Society for Horticultural Science, 119:2, 361-366 (1994), Zhang, Z., et al. J. Amer. Soc. Hort. Sci. 122(3): 300-305 (1997). *A. tumefaciens* and *A. rhizogenes* are plant pathogenic soil bacteria which genetically transform plant cells. The Ti and R1 plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Despite the fact the host range for *Agrobacterium*-mediated transformation is broad, some major cereal or vegetable crop species and gymnosperms have generally been recalcitrant to this mode of gene transfer, even though some success has recently been achieved in rice and corn. Hiei et al., The Plant Journal 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, January), 165-169 (1993), Aragao, F. J. L., et al. Plant Mol. Biol. 20(2, October), 357-359 (1992), Aragao Theor. Appl. Genet. 93:142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992)

Another method for physical delivery of DNA to plants is sonication of target cells. Zhang et al., Bio/Technology 9:996 (1991). Alternatively, liposome or spheroplast fusions have been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts and whole cells and tissues have also been described. Saker, M.; Kuhne, T. Biologia Plantarum 40(4): 507-514 (1997/98), Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994).

Following transformation of tomato target tissues, expression of the above-described selectable marker genes allows for preferential selection of transformed cells, tissues and/or plants, using regeneration and selection methods now well known in the art. The foregoing methods for transformation would typically be used for producing a transgenic line. The transgenic line could then be crossed, with another (non-transformed or transformed) line, in order to produce a new transgenic tomato line. Alternatively, a genetic trait which has been engineered into a particular tomato cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term tomato plant, cultivar or tomato line is used in the context of the present invention, this also includes any single gene conversions of that cultivar or line. The term single gene converted plant as used herein refers to those garden tomato plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term backcrossing as used herein refers to the repeated crossing of a hybrid progeny back to one of the parental tomato plants for that line. The parental tomato plant that contributes the gene for the desired characteristic is termed the nonrecurrent or 'donor parent'. This terminology refers to the fact that the nonrecurrent parent is used only once when generating the original hybrid plant and therefore does not recur. The parental tomato plant to which the gene or genes from the donor parent are transferred is known as the 'recurrent parent' as it is used for several rounds in the backcrossing protocol (Poehlman & Sleper, 1994; Fehr, 1987). In a typical backcross breeding program, the original cultivar of interest (recurrent parent) is crossed to a second line (donor parent) that carries the single gene (or genes) of interest to be transferred. The resulting progeny from this cross are then crossed again to the recurrent parent and the process is repeated until an acceptable garden tomato plant is obtained wherein essentially all of the desired morphological and physiological characteristics of the recurrent parent are recovered in the converted plant, in addition to the single transferred gene from the nonrecurrent parent.

The choosing (or choice) of a suitable recurrent parent is an important step for a successful backcross breeding program. The goal of a backcross breeding protocol is to alter or substitute a single trait or characteristic in the original line. To accomplish this, a single gene of the recurrent cultivar is modified or substituted with the desired gene from the donor parent, while retaining essentially all of the rest of the desired genetic, and therefore the desired physiological and morphological, constitution of the original line. The choice of the particular nonrecurrent parent depends on the purpose of the backcross breeding. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the self-progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, herbicide resistance (such as bar or pat genes), resistance for bacterial, fungal, or viral disease such as gene I used for BCMV resistance), insect resistance, enhanced nutritional quality (such as 2s albumine gene), industrial usage, agronomic qualities such as the "persistent green gene", yield stability and yield enhancement. These genes are generally inherited through the nucleus. Some other single gene traits are described in U.S. Pat. Nos. 5,777,196, 5,948,957 and 5,969,212, the disclosures of which are specifically hereby incorporated by reference.

All references cited herein are incorporated by reference in the application in their entireties.

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

Deposits

A deposit of LA2093, is and has been maintained by The Pennsylvania State University, University Park, Pa. 16802 since prior to the filing date of this application. Access to this deposit has been made available during the pendency of the application to the Commissioner of Patents and Trademarks and persons determined by the Commissioner to be entitled thereto upon request. Applicant(s) have made available to the public without restriction a deposit of at least 2500 seeds of each variety or line with the American Type Culture Collection (ATCC), Rockville, Md., 20852, Deposit No. PTA-120390 on May 31, 2013. The seeds deposited with the ATCC were taken from the same deposit maintained at The Pennsylvania State University as described above. Additionally, Applicant has met all the requirements of 37 C.F.R. §1.801-1.809, including providing an indication of the viability of the sample when the deposit is made. This deposit of the aforementioned tomato varieties or lines will be maintained in the ATCC Depository, which is a public depository, for a period of 30 years, or 5 years after the most recent request, or for the enforceable life of the patent, whichever is longer, and will be replaced if it ever becomes nonviable during that period. Applicant will impose no restrictions on the availability of the deposited material from the ATCC; however, Applicant has no authority to waive any restrictions imposed by law on the transfer of biological material or its transportation in commerce.

EXAMPLES

In search of genetic sources of high fruit lycopene content in tomato, we acquired seeds of, and grew and evaluated under field conditions, >300 wild tomato accessions. This experiment led to the identification and selection of one accession of wild species *Solanum pimpinellifolium* with exceptionally high fruit lycopene content.

The lycopene concentration of this accession is as high as 390 μg/g fresh tomato tissue, approximately 10-fold that of the commercial cultivars of tomato (~30-60 μg/g fresh fruit tissue). The *Solanum pimpinellifolium* selection which was discovered to have exceptionally high fruit lycopene content is designated as LA2093.

With the goal of transferring this desirable trait to the cultivated (normal) tomato, this accession was hybridized with a cultivated tomato *Solanum lycopersicum* and $F_1$ progeny produced. The $F_1$ progeny were self-crossed and produced $F_2$ progeny. The $F_2$ progeny were grown under field conditions and evaluated for fruit lycopene content. From this point on, two projects were pursued simultaneously to 1) identify and genetically map the genes (QTLs) contributing to the high fruit lycopene concentration, and 2) develop commercially acceptable tomato breeding lines and cultivars with high fruit lycopene concentration. The mapping project, which involved development and use of various filial populations, including $F_2$, $F_3$, $F_4$, $F_5$, $F_6$, $F_7$, $F_8$, $F_9$ and $F_{10}$, by self-crossing in successive generations, resulted in the identification, mapping and verification of a few genomic locations (also knows an quantitative trait loci or QTLs), including two on *Solanum pimpinellifolium* LA2093 chromosomes 7 and 12, with significant effects on tomato fruit lycopene concentration (see below for details). The second project encompassed genetic development of different types of fresh-market and processing tomatoes with high fruit lycopene content. Here, two approaches were taken. One was growing and evaluating plants for fruit lycopene content in successive filial generations (i.e., $F_2$, $F_3$, $F_4$, $F_5$, $F_6$, $F_7$, $F_8$, $F_9$ and $F_{10}$) under field conditions and in each generation selecting plants with the highest fruit lycopene content. This approach resulted in development of cherry tomatoes (round fruits with diameter of 1.5-3 cm) with exceptionally high fruit lycopene content. The second approach involved backcrossing the selected $F_2$ plants, which contained highest fruit lycopene content, with different *Solanum lycopersicum* genotypes for several generations alternated and followed by several generations of self-crossing and intensive selection. This approach, which took about 10 years, resulted in the development of different types of fresh-market (e.g. grape, plum and medium/large round fruit) and processing tomato lines with high fruit lycopene contents (see below for details). The concentration of fruit lycopene in these new lines ranges from 100 to 200 μ/g fresh fruit tissue, much higher than what can be found in current commercial breeding lines and cultivars.

The plants of the present invention can also be produced by protoplast fusion. To produce plants by protoplast fusion, a protoplast from the selected *Solanum pimpinellifolium* plant (LA2093) that is high in fruit lycopene content is obtained along with a protoplast from a *Solanum lycopersicum*. The protoplasts are then fused using standard protoplast fusion procedures, which are well known in the art. The resulting allogeneic cells are obtained and regenerated into plants, which are evaluated for fruit lycopene concentration. Plants high in fruit lycopene concentration are identified and selected and self- or cross-hybridized, as described above.

The *Solanum lycopersicum* plants produced according to the method of this invention produce fruits with exceptionally high content of lycopene when grown in the field or under greenhouse conditions. These plants contain genomic locations (QTLs) for high fruit lycopene content incorporated from the selected *Solanum pimpinellifolium* accession (LA2093), including, but not limited to, two QTLs on chromosome 7 and 12.

The present invention involves the creation of tomato plants (*Solanum lycopersicum*) that are exceptionally high in fruit lycopene content. The plants of the present invention are new and novel because they are exceptionally high in fruit lycopene content, when compared to normal commercial breeding lines and cultivars of tomato. The plants of the present invention also have many other desirable horticultural characteristics, which have been incorporated from various resources.

The inventor of the present invention has discovered *Solanum pimpinellifolium* plants that contain genes for high fruit lycopene content. These *Solanum pimpinellifolium* plants can be used to create tomato plants (*Solanum lycopersicum*) that are high in fruit lycopene content. For example, *Solanum pimpinellifolium* plants designated as LA2093 were used to create the plants of the present invention. *Solanum pimpinellifolium* plants designated as LA2093 have also been referred to as PSLP125 by the inventor. Seeds of LA2093 (PSLP125) were deposited with the American Type Culture Collection, 12301 Parklawn Drive, Md. 20852, under the provisions of the Budapest Treaty. The seeds were deposited on May 31, 2013 and received ATCC Accession Number #PTA-120390. In addition, LA2093 (PSLP125) is also available from the CM Rick Tomato Genetic Resource Rick Center at the University of California-Davis, Davis, Calif. upon request.

The inventor has discovered that LA2093 plants produce fruits with exceptionally high fruit lycopene content (300-390 μg/g fresh tomato tissue). Prior to this discovery, high fruit lycopene content of plants designated as LA2093 had been UNKNOWN. *Solanum pimpinellifolium* plants designated as LA2093 contain genes (QTLs) which contribute to its high fruit lycopene content. However, one skilled in the art would recognize that any *Solanum pimpinellifolium* which contains the desirable genes (QTLs) for high lycopene and has fruit with high lycopene content can be used in this invention.

The plants of the present invention can be developed by traditional breeding protocols. For example, seed from *Solanum pimpinellifolium* plants designated as LA2093 can be used. Seeds of LA2093 are planted in a greenhouse or in a field. The resulting plants are allowed to grow, produce flowers, set fruit and reach maturity (i.e., produce ripe fruit). After fruits are ripen, they are harvested and examined for lycopene content and based on the results plants with highest level of lycopene contents are selected. Fruit lycopene content can be determined by different procedures, including: A. R. DAVIS, W. W. FISH, P. PERKINS-VEAZIE (2003) *A Rapid Hexane-free Method for Analyzing Lycopene Content in Watermelon Journal of Food Science* 68 (1), 328-332; andHyman J R, J Gaus, and M R Foolad. 2004. *A rapid and accurate method for*

*estimating tomato lycopene content by measuring chromaticity values of fruit puree. JASHS* 129: 717-723.

The *Solanum pimpinellifolium* accession LA2093 plants that exhibit the highest concentrations of fruit lycopene are selected and crossed with cultivated tomato plants (*Solanum lycopersicum*) by placing the pollen from a selected LA2093 plant on the stigma of a cultivated tomato plant. After the tomato fruit develops, seeds are collected. The seeds ($F_1$ generation) are grown to produce $F_1$ plants in the greenhouse or under field conditions, which are evaluated for fruit lycopene content. $F_1$ plants with highest fruit lycopene concentrations are selected. A selected $F_1$ plant with the highest fruit lycopene content is self-pollinated (i.e., self-hybridized). After the tomato fruit develops on the $F_1$ plant, seeds are collected. The seeds ($F_2$ generation) are grown to produce $F_2$ plants under field conditions. At this point two different procedures are taken to 1) identify and map genes for high fruit lycopene content, and 2) develop tomato breeding lines and cultivars with high fruit lycopene content and other desirable horticultural characteristics for commercial use, as described below.

1) Mapping Fenes (Aka as Quantitative Trait Loci, QTLs) Contributing to High Fruit Lycopene Content:

To identify and map genes (QTLs) for fruit lycopene content, successive filial populations, including $F_2$, $F_3$, $F_4$, $F_5$, $F_6$, $F_7$, $F_8$, $F_9$ and $F_{10}$, were developed by self-crossing (self-hybridizing) in successive generations. Two genetic linkage maps were developed, one based on the $F_2$ population and one based on the $F_7$ generation. To identify and map genes (QTLs) for high fruit lycopene content in the *Solanum pimpinellifolium* accession LA2093, plants of the $F_2$, $F_3$, $F_4$, $F_5$, $F_6$, $F_7$, $F_8$, $F_9$ and $F_{10}$ were evaluated for fruit lycopene contents in replicated trials in different years. The $F_2$ genetic map was used to identify and map fruit quality QTLs in $F_2$, $F_3$ and $F_4$ generations and the $F_7$ genetic map was used to identify and map fruit quality QTLs in $F_7$, $F_8$, $F_9$ and $F_{10}$ generations. The mapping strategies resulted in the identification and mapping of several QTLs for high fruit lycopene contents on different chromosomes of the *Solanum pimpinellifolium* accession LA2093, including two consistent and large-effect QTLs on chromosomes 7 and 12. It is the understanding of the inventor that these two QTLs from *Solanum pimpinellifolium* accession LA2093 have major effect on tomato fruit lycopene content and are essential for the development of high fruit lycopene tomatoes, as described in this invention.

2) Development of Tomato Breeding Lines with High Fruit Lycopene Content and Other Desirable Horticultural Characteristics:

Two approaches were taken to transfer genes (QTLs) for high fruit lycopene content from *Solanum pimpinellifolium* accession LA2093 to the cultivated tomato (*Solanum lycopersicum*) and develop breeding lines with high fruit lycopene content:

In the first approach, following evaluation of the $F_2$ population in the field for fruit lycopene content (using techniques described above), plants with highest concentrations of fruit lycopene as well as with other desirable horticultural characteristics were identified and selected. The selected plants were self-crossed to produce $F_3$ generation. The $F_3$ plants were grown under field conditions the next year and similar evaluation/characterization and selection practices were conducted. This practice was continued for the next several generations, including $F_4$, $F_5$, $F_6$, $F_7$, $F_8$, $F_9$ and $F_{10}$ Throughout the breeding process and in every generation, intensive selections were made for high fruit lycopene content as well as many other desirable horticultural characteristics, including fruit size, fruit shape, plant type, growth habit, maturity, disease resistance and yield. The end results were development of cherry tomato breeding lines (round fruits with diameter of 1.5-3 cm) with exceptionally high fruit lycopene content (fruit lycopene content of up to 200 µg/g fresh tomato tissue) and other desirable horticultural characteristics. These "cherry" tomato breeding lines are available for commercial release and production of hybrid cultivars. In fact, some are currently used to develop experimental hybrids, which may be commercialized.

In the second approach, modified backcross breeding protocols were employed to develop different types of fresh-market and processing tomatoes with high fruit lycopene content as well as with other desirable horticultural characteristics. Briefly, in the $F_2$ generation, following the identification and selection of plants with the highest levels of fruit lycopene content and other desirable horticultural characteristics, the selected plants were cross hybridized with different *Solanum lycopersicum* breeding lines and cultivars, including genotypes of both fresh-market and processing tomato backgrounds with good horticultural characteristics, and different $BC_1$ (first backcross) populations were developed. Subsequently, plants of the $BC_1$ generation were grown under field conditions (the next year) and evaluated for fruit lycopene content as well as other horticultural characteristics. Plants with high fruit lycopene content and other desirable characteristics were selected and self-crossed (self-hybridized) to produce $BC_1S_1$ generation. The $BC_1S_1$ populations were subsequently evaluated for fruit lycopene content and other horticultural characteristics. Plants with high fruit lycopene content and other desirable horticultural characteristics were identified and selected. The selected plants were hybridized with different *Solanum lycopersicum* breeding lines with complementary characteristics, including genotypes of both fresh-market and processing backgrounds, and different $BC_2$ (second backcross) populations were developed. This modified backcross breeding program was continued for several more generations followed by a few generations of self-breeding and intensive selection to develop inbred lines of different types of fresh market (e.g. cherry, grape, plum and medium and large round fruit) and processing tomatoes with high fruit lycopene content and other desirable horticultural characteristics. The concentration of fruit lycopene in these new lines ranges from 100 to 200 µg/g fresh fruit tissue, much higher than what can be found in current commercial breeding lines and cultivars. The new tomato breeding lines are available for commercial release and production of hybrid cultivars.

It is important to note that *Solanum lycopersicum* is cleistogamous. Therefore, it is very unlikely in the wild that cross pollination between *Solanum pimpinellifolium* and *Solanum lycopersicum* would occur without human technical intervention. It is also unlikely that the identification, selection and backcrossing for the genes (QTLs) for high fruit lycopene content would occur naturally.

It should also be noted that protoplast fusion can also be used to create the plants of the present invention. To produce plants by protoplast fusion, a protoplast from the selected *Solanum pimpinellifolium* plant (LA2093) which is high in fruit lycopene content is obtained along with a protoplast from a *Solanum lycopersicum*. The protoplasts are then fused using standard protoplast fusion procedures, which are well known in the art. Different protocols for protoplast fusion can be employed as described in the literature. The resulting allogenic cells are obtained and regenerated into plants which are evaluated for fruit lycopene concentration. Plants high in fruit lycopene concentration are identified and selected and self- or cross-hybridized, as described above.

References

Di Mascio P, Devasagayam T P, Kaiser S, Sies H (1990) Carotenoids, tocopherols and thiols as biological singlet molecular oxygen quenchers. Bioch Soc Trans 18: 1054-1056.

FAOSTAT (2005) FAO Statistical Databases. Food and agriculture organization of the United Nations, Statistics Division Gerster H (1997). The potential role of lycopene for human health. J Amer Coll Nutri 16; 109-126.

Giovannucci E (1999) Tomatoes, tomato-based products, lycopene, and cancer; Review of the epidemiologic literature. J Natl Cancer Inst 91:317-331.

Giovannucci E, Clinton S K (1998) Tomatoes, lycopene, and prostate cancer. Proc Soc Exp Biol Med 218; 129-139

Nguyen M L, Schwartz S J (1999) lycopene: chemical and biological properties. Food Tech 53:38-45.

Palmieri S, Martiniello P, Soressi G P (1978) Chlorophyll and carotene content in high pigment and green flesh fruits. Rep Tomato Genet Coop 28: 10

Rick C M (1980) Tomato. Hybridization of Crop Plants. Am. Soc. Agron./Crop Sci. Soc. Am., Madison, Wis., USA, pp 669-680.

Ronen G, Carmel-Goren L, Zamir D, Hirschberg J (2000). An alternative pathway to beta-carotene formation in plant chloroplast discovered by map-based cloning of Beta and old-gold color mutation in tomato. Proc Natl Acad Sci USA 97; 11102-11107.

Sies H, Stahl W (1998) Lycopene: Antioxidant and biological effects and its bioavailability in the human. Proc Soc Exp Biol Med 218:121-124.

Soressi G P (1975) New spontaneous or chemically-induced fruit-ripening tomato mutants. Rprt Tomato Genetic Coop 25:21-22.

Thompson A E, Hepler R W, Kerr E A (1962) Clarification of the inheritance of high total carotenoid pigments in the tomato. Proc Am Soc Hort Sci 81; 434-442.

Thompson A E, Tomes M L, Erickson H T, Wann E V, Armstrong R J (1967) Inheritance of crimson fruit color in tomatoes. Proc Am Soc Hort Sci 91:495-504.

Tsubono Y, Tsugane S, Gey KF (1999) Plasma antioxidant vitamins and carotenoids in five Japanese populations with varied mortality from gastric cancer. Nutri Cancer 34; 56-61 USDA (2005) Agricultural statistics 2005. United State Department of Agriculture, National Agricultural Statistics Service van Tuinen A, Cordommier-Pratt M-M, Pratt LH, Verkerk R, Zabel P, Koornneef M (1997) The mapping of phytochrome genes and photomorphogenic mutants of tomato. Theor Appl Genet 94; 115-122.

Vinson J, Hao Y, Su X, Zubik L (1998) Phenol antioxidant quantity and quality in foods: vegetables. J Agri Food Chem 46:3630-3634.

Wann E V (1995) Reduced plant growth in tomato mutants high pigment and dark green partially overcome by gibberellin. HortScience 30; 379.

Willcox J K, Catignani G L, Lazarus S (2003) Tomatoes and cardiovascular health. Crit Rev Food Sci Nutr 43:1-18

Yen H C, Shelton B A, Howard L R, Lee S, Vrebalov J, Giovannoni J J (1997) The tomato high pigment(hp) locus maps to chromosome 2 and influences plastome copy number and fruit quality. Theor Appl Genet 95:1069-1079.

What is claimed is:

1. A high lycopene content of greater than 100 µg/g fresh tomato tissue Solanum lycopersicum plant or part thereof, having within its genome a QTL associated with high lycopene content on chromosome 7 and a QTL associated with high lycopene content on chromosome 12, of Solanum pimpinellofolium LA2093 having ATCC Accession No. PTA-120390, wherein said QTL is not in said Solanum lycopersicum natural genetic background, and wherein the location of said QTL on chromosome 7 is indicated by a genomic region bound by genetic markers cTOS19O5 and cLEN14F9 and said QTL on chromosome 12 is indicated by a genomic region bound by genetic markers OH275 and T0800.

2. A plurality of tomato seeds descended from the plant of claim 1 which retain the QTLs of claim 1, wherein plants grown from said seeds have a fruit tissue lycopene content greater than 100 µg/g fresh tomato tissue and wherein said fruit tissue lycopene content of said plants grown from seeds descended from the plant of claim 1 is not statistically different from the fruit tissue lycopene content of the plant of claim 1 when grown in the same environment.

3. A method of producing a high lycopene Solanum lycopersicum tomato plant, having a lycopene content of greater than 100 µg/g fresh tomato tissue comprising:
   providing a high lycopene Solanum pimpinellofolium LA2093 having ATCC Accession No. PTA-120390 donor plant;
   transferring a nucleic acid from said donor plant to one or more Solanum lycopersicum tomato plants, wherein the transfer results in the introduction of genomic materials from the donor plant in the corresponding region of the genome of one or more recipient plants; and
   selecting from amongst said recipient tomato plants a plant that comprises within its genome a QTL for high lycopene content, from Solanum pimpinellofolium LA2093 on chromosomes 7 and 12, wherein said selection comprises detecting on chromosomes 7 and 12 a genetic marker linked to said QTL for high lycopene content, wherein the location of said QTL on chromosomes 7 and 12 of said plant is indicated by a genomic region bounded by and comprising the genetic markers cTOS 19O5 and cLEN14F9, and OH275 and T0800, respectively.

4. A method of developing a tomato plant in a tomato plant breeding program using plant breeding techniques comprising:
   introgressing into a tomato plant the trait of high lycopene content from the plant of claim 1 as a source of breeding material, thereby creating a descendant plant with lycopene content from the plant of claim 1 and comprising the QTLs associated with lycopene content from Solanum pimpinellofolium LA2093, and thereafter
   selecting said descendant tomato plant having the lycopene trait.

5. A Solanum lycopersicum tomato plant, or a part thereof, having within its genome a QTL on chromosome 7 and a QTL on chromosome 12, of Solanum pimpinellofolium LA2093 associated with high lycopene content, wherein said QTL is not in said Solanum lycopersicum natural genetic background, wherein the location of said QTL on chromosome 7 is indicated by a genomic region bound by genetic markers cTOS 19O5 and cLEN14F9 and said QTL on chromosome 12 is indicated by a genomic region bound by genetic markers OH275 and T0800, and wherein said plant is produced by growing the seed of claim 2.

6. Pollen or an ovule of the plant of claim 5, said pollen or ovule having within its genome a QTL on chromosome 7 and a QTL on chromosome 12, of Solanum pimpinellofolium LA2093 associated with high lycopene content, wherein said QTL is not in said Solanum lycopersicum natural genetic background, wherein the location of said QTL on chromosome 7 is indicated by a genomic region bound by genetic markers cTOS19O5 and cLEN14F9 and said QTL on chromosome 12 is indicated by a genomic region bound by genetic markers OH275 and T0800.

7. A fruit of the plant of claim 5, said fruit having within its genome a QTL on chromosome 7 and a QTL on chromosome 12, of *Solanum pimpinellofolium* LA2093 associated with high lycopene content, wherein said QTL is not in said *Solanum lycopersicum* natural genetic background, wherein the location of said QTL on chromosome 7 is indicated by a genomic region bound by genetic markers cTOS19O5 and cLEN14F9 and said QTL on chromosome 12 is indicated by a genomic region bound by genetic markers OH275 and T0800.

8. A method for producing a hybrid *Solanum lycopersicum* seed comprising: crossing a first parent tomato plant with a second parent tomato plant and harvesting the resultant hybrid tomato seed, said seed having within its genome a QTL on chromosome 7 and a QTL from chromosome 12, of *Solanum pimpinellofolium* LA2093 associated with high lycopene content, wherein said QTL is not in said *Solanum lycopersicum* natural genetic background, wherein the location of said QTL on chromosome 7 is indicated by a genomic region bound by genetic markers cTOS19O5 and cLEN14F9 and said QTL on chromosome 12 is indicated by a genomic region bound by genetic markers OH275 and T0800, and wherein said first or second parent tomato plant is the tomato plant of claim 5.

9. A method of producing a tomato fruit comprising:
 a) growing the tomato plant of claim 5 to produce a tomato fruit, and
 b) harvesting said tomato fruit.

10. A method of vegetatively propagating a tomato plant comprising:
 a) collecting part of the plant according to claim 5;
 b) obtaining a plantlet from said part.

11. The method according to claim 10, further comprising growing a plant from said plantlet.

12. The method according to claim 11, further comprising harvesting a fruit from said plant grown from said plantlet.

* * * * *